United States Patent [19]

Shaw

[11] Patent Number: 5,283,368

[45] Date of Patent: Feb. 1, 1994

[54] PROCESS FOR PRODUCING ALKOXYLATED THIO-COMPOUNDS

[75] Inventor: James E. Shaw, Bartlesville, Okla.

[73] Assignee: Phillips Petroleum Company, Bartlesville, Okla.

[21] Appl. No.: 6,278

[22] Filed: Jan. 19, 1993

[51] Int. Cl.$^5$ .......................................... C07C 319/14
[52] U.S. Cl. ........................................ 568/45; 568/55
[58] Field of Search .................................... 568/45, 55

[56] References Cited

U.S. PATENT DOCUMENTS

| | | | |
|---|---|---|---|
| 2,570,050 | 10/1951 | Eby | 260/609 |
| 2,570,051 | 10/1951 | Eby | 167/22 |
| 2,776,997 | 1/1957 | Doumani | 568/55 |
| 3,775,483 | 11/1973 | Frederickson et al. | 260/609 R |
| 4,575,569 | 3/1986 | Edwards | 568/45 |
| 4,876,389 | 10/1989 | Gongora et al. | 568/45 |

Primary Examiner—Marianne M. Cintins
Assistant Examiner—Margaret J. Page
Attorney, Agent, or Firm—Lucas K. Shay

[57] ABSTRACT

A composition comprising a base and an alkoxylated compound selected from the group consisting of an alkoxylated alcohol, alkoxylated mercaptan, and mixtures thereof can be used to catalyze the reaction of a sulfur-containing compound such as, for example, n-octyl mercaptan, or hydrogen sulfide, and an alkylene oxide such as, for example, propylene oxide to produce an alkoxylated thio-compound such as, for example, n-octyl mercaptan monopropoxylate or 1-mercapto-2-propanol.

19 Claims, No Drawings

PROCESS FOR PRODUCING ALKOXYLATED THIO-COMPOUNDS

FIELD OF THE INVENTION

This invention relates to a catalyst and a process for the production of an alkoxylated thio-compound and derivatives thereof by a catalyzed reaction of an alkylene oxide and a mercaptan or hydrogen sulfide.

BACKGROUND OF THE INVENTION

It is well-known that the addition products of an alkylene oxide and a mercaptan or hydrogen sulfide can be used, for example, in diesel fuels to improve octane number, as a surfactant for industrial applications, as an additive for transmission fluids, as lubricating oil additive, and as an insecticide such as fly repellents. Conventionally, the addition products or alkoxylated thio-compounds, are produced by reacting an alkylene oxide with a mercaptan or hydrogen sulfide catalyzed by an alkaline catalyst such as a hydroxide of an alkali metal or a hydroxide of an alkaline earth metal or an alkyl-substituted ammonium hydroxide. See U.S. Pat. Nos. 2,570,050 and 2,570,051. An alkaline catalyst such as sodium hydroxide in methanol has also been used as a catalyst for the reaction of an alkylene oxide and mercaptan. See U.S. Pat. No. 3,775,483.

The above-described processes, however, was found to have a lag period, i.e., no reaction initially, especially at low temperatures, i.e., lower than about 70° C. Consequently, more alkylene oxide needs to be added to the reaction mixture to initiate the reaction. However, the excess amount of alkylene oxide added generally causes too vigorous and too exothermic reactions. A "too vigorous" reaction is one that the reaction mixture boils out of reactor and a "too exothermic" reaction is one that the temperatures of the reaction cannot be maintained below the highest temperature that is permissible. This too vigorous and too exothermic reaction is termed herein as runaway reaction. In order to avoid this runaway reaction so that a process can be carried out at lower temperatures to obtain a greater selectivity toward the desired product, a new process needs to be developed.

SUMMARY OF THE INVENTION

An object of the present invention is to provide a composition that can be used to catalyze the reaction of an alkylene oxide and a mercaptan or hydrogen sulfide. Another object of the invention is to provide a process for preparing the catalyst composition. A further object of the invention is to provide a process for the reaction of an alkylene oxide and a mercaptan or hydrogen sulfide, using the inventive composition as catalyst. Still another object of the invention is to provide a high productivity process for producing an alkoxylated thio-compound. An advantage of the invention is that the inventive composition is more soluble in an organic reaction medium. Another advantage is that the inventive process improves the reactivity of the reactants. Other objects, advantages, features, and aspects will become more apparent as the invention is more fully disclosed hereinbelow.

According to the present invention, a process for producing an alkoxylated thio-compound is provided which comprises contacting an alkylene oxide with a sulfur-containing compound in the presence of a catalyst under conditions sufficient to synthesize the alkoxylated thio-compound where the sulfur-containing compound has the formula of R—SH wherein R is selected from the group consisting of hydrogen, a hydrocarbyl radical having 1 to about 20 carbon atoms, and mixtures thereof; the catalyst comprises a base and an alkoxylated compound selected from the group consisting of an alkoxylated mercaptan, an alkoxylated alcohol, and mixtures thereof.

DETAILED DESCRIPTION OF THE INVENTION

An alkoxylated thio-compound can be prepared by the reaction of an alkylene oxide and a sulfur-containing compound catalyzed by a catalyst. The reaction can be depicted as

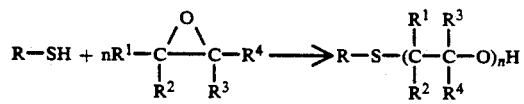

where R, $R^1$, $R^2$, $R^3$, and $R^4$ can be the same or different and are each selected from the group consisting of hydrogen, a $C_1$-$C_{20}$ hydrocarbyl radical, and mixtures thereof. The hydrocarbyl radical is further selected from the group consisting of an alkyl radical, aryl radical, cycloalkyl radical, alkylaryl radical, arylalkyl radical, alkenyl radical, and mixtures thereof; n is a number from 1 to about 20.

Examples of suitable mercaptan having the formula of R—SH include, but are not limited to, hydrogen sulfide, methyl mercaptan, ethyl mercaptan, n-propyl mercaptan, n-butyl mercaptan, t-butyl mercaptan, n-hexyl mercaptan, cyclohexyl mercaptan, n-octyl mercaptan, nonyl mercaptan, t-nonyl mercaptan, n-decyl mercaptan, dodecyl mercaptan, t-dodecyl mercaptan, t-tetradecyl mercaptan, phenyl acetyl mercaptan, p-methyl phenyl mercaptan, and mixtures thereof. The presently preferred mercaptan is octyl mercaptan.

Examples of suitable alkylene oxide having the formula of

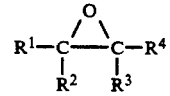

include, but are not limited to, ethylene oxide, propylene oxide, 1,2-epoxycyclohexane, 2-methyl-1,2-epoxypropane, 2,3-epoxybutane, 3-methyl-1,2-epoxybutane, 2-methyl-2,3-epoxybutane, 2,3-epoxyhexane, 3,3-methyl-1,2-epoxybutane, and mixtures thereof. The presently preferred alkylene oxides are ethylene oxide and propylene oxide.

The alkoxylated thio-compound that can be produced by the process of the invention has the formula of

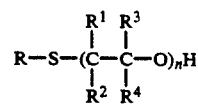

where R, $R^1$, $R^2$, $R^3$, $R^4$ and n are the same as those described above. Examples of alkoxylated thio-compound that can be prepared by the process of the present invention include, but are not limited to, 2-mercaptoethanol, 1-mercapto-2-propanol, 2-(ethylthio)ethanol, 2-hydroxyethyl n-octyl sulfide, 2-methyl-2-hydroxypropyl n-octyl sulfide, 2-hydroxybutyl n-octyl sulfide, 2-hydroxyhexyl n-octyl sulfide, 2-hydroxy-3,3-dimethylbutyl n-octyl sulfide, 2-hydroxybutyl n-octyl sulfide, 2-hydroxy-3-methylbutyl n-octyl sulfide, 2-hydroxypropyl n-octyl sulfide, n-octyl mercaptan monoethoxylate having the formula of $CH_3-(CH_2)_7-S-CH_2CH_2OH$ (such as for example, 2-hydroxyethyl n-octyl sulfide), n-octyl mercaptan diethoxylate having the formula of $CH_3-(CH_2)_7-S-(CH_2CH_2O)_2H$, n-octyl mercaptan triethoxylate having the formula of $CH_3-(CH_2)_7-S-(CH_2CH_2O)_3H$, n-octyl mercaptan monopropoxylate having the formula of $CH_3-(CH_2)_7-S-CH(CH_3)CH_2OH$ (2-hydroxy-1-methylethyl n-octyl sulfide) or $CH_3-(CH_2)_7-S-CH_2CH(CH_3)OH$ (2-hydroxypropyl n-octyl sulfide), t-dodecyl sulfenyl polyethylene oxide having the formula of $t-C_{12}H_{25}-S-(CH_2CH_2O)_nH$ wherein n is a number from 1 to about 20, and mixtures thereof. Tert-dodecyl sulfenyl polyethylene oxide is commercially available from Phillips Petroleum Company, Bartlesville, Okla.

Derivatives of the alkoxylated thio-compound can be prepared by reacting the alkoxylated thio-compound prepared by the process of the invention with acids, acid halides and acid anhydrides. Examples of some of the derivatives which are useful as plasticizers, oxidation inhibitors, wetting agents, textile aids, detergents, insecticides and fungacides are halides, acetates, sulfates, benzoates, sulfonates, xanthates, phosphonate, acrylates, etc.

According to the invention, the catalyst useful for the process of the invention comprises a base and an alkoxylated compound selected from the group consisting of an alkoxylated mercaptan, an alkoxylated alcohol, and mixtures thereof. The base useful for the catalyst can be an organic or an inorganic base, or mixtures thereof. Suitable organic bases include, but are not limited to tetramethylammonium hydroxide, tetraethylammonium hydroxide, tetrapropylammonium hydroxide, tetramethylammonium bisulfide, tetraethylammonium bisulfide, and mixtures of any two or more thereof. Suitable inorganic bases include, but are not limited to, lithium hydroxide, sodium hydroxide, potassium hydroxide, calcium hydroxide, magnesium hydroxide, sodium bicarbonate, sodium carbonate, sodium oxide, sodium sulfide, sodium bisulfide, magnesium oxide, calcium oxide, calcium carbonate, sodium phenoxide, barium phenoxide, calcium phenoxide, $R^5ONa$, $R^5SNa$, and mixtures of any two or more thereof; where R is a $C_1-C_{18}$ alkyl radical. Presently, an inorganic base is preferred because of availability and low cost of inorganic bases. Among the inorganic bases, sodium hydroxide is preferred because it is readily available and inexpensive.

The alkoxylated alcohol useful in the present invention has a general formula of $R^6O[CH_2CH(R^7)O]_nH$ where $R^6$ is a $C_1-C_{20}$ hydrocarbyl radical selected from the group consisting of alkyl radical, alkylaryl radical, aryl radical, cycloalkyl radical and alkenyl radical; Preferably $R^6$ is a $C_6-C_{18}$ alkyl radical. Most preferably $R^6$ is a $C_{10}-C_{16}$ alkyl radical; $R^7$ is selected from the group consisting of hydrogen, $C_1-C_{16}$ alkyl radicals, and $C_2-C_{16}$ alkenyl radicals; and n is a number of from 1 to about 20, preferably from about 2 to about 12, most preferably from 5 to 10. Generally $R^7$ can contain from 0 to about 16 carbon atoms. Preferably $R^7$ is a hydrogen or a $C_1-C_3$ alkyl radical. Most preferably $R^7$ is a hydrogen. An example of suitable alkoxylated alcohol is TERGITOL ® 15-S-7 which is an ethoxylated alcohol, is manufactured and marketed by Union Carbide Corporation, and has the formula of $R^6O(CH_2CH_2O)_7H$ where $R^6$ is a secondary alkyl radical having 11-15 carbon atoms and 7 is an averaged number of the ethylene oxide units. Another example is an ethoxylated phenol having the same number of ethylene oxide units. Other alkoxylated alcohols are also available from Union Carbide Corporation.

The alkoxylated mercaptan useful in the present invention has a general formula of $R^6S[CH_2CH(R^7)O]_nH$ where $R^6$ and $R^7$ are the same as those described above. An example of an alkoxylated mercaptan is an ethoxylated mercaptan having the formula of $R^6S(CH_2CH_2O)_7H$ where $R^6$ is primarily a tertiary dodecyl group and 7 is an averaged number of ethylene oxide units. This ethoxylated mercaptan is a surfactant commercially available from Phillips Petroleum Company, Bartlesville, Okla. under the trade name AQUACLEEN ® II. Another example is an ethoxylated thiophenol having the same number of ethylene oxide units. Other alkoxylated mercaptans are also available from Phillips Petroleum Company.

The weight ratio of the alkoxylated alcohol or alkoxylated mercaptan to base can vary widely, preferably from about 1:1 to about 1000:1, most preferably from about 20:1 to 50:1 for best results.

The catalyst can be made by properly mixing the components in the ratio described above employing any suitable mixing means such as shaking or stirring. The catalyst also can be formed in-situ by adding a base and either an alkoxylated alcohol or an alkoxylated mercaptan before or during the contacting of mercaptans and alkylene oxides. However, it is preferably prepared by heating the mixture of the alkoxylated alcohol or alkoxylated mercaptan and the base, in the presence or absence of a solvent at a temperature in the range of from about 40° C. to about 150° C., preferably from 60° C. to 100° C. for from about 10 minutes to about 5 hours, preferably from 30 minutes to 2 hours. The heating is preferably carried out under an inert gas such as nitrogen and can be under any pressure, preferably under about 1 atmosphere to about 2 atmospheres.

The suitable conditions for the contacting of a mercaptan or hydrogen sulfide with an alkylene oxide include a temperature in the range of from about 20° C. to about 250° C., preferably from 50° C. to 150° C. and a time of from about 10 minutes to about 10 hours, preferably 30 minutes to 5 hours. The pressure can vary widely from about 1 atmosphere to about 30 atmospheres, preferably from about 1 atmosphere to about 3 atmospheres.

Generally, one of the reactants, either the sulfur-containing compound (mercaptan or hydrogen sulfide) or alkylene oxide, is slowly added to the other reactant in the presence of the catalyst described above. Usually the alkylene oxide is added to the sulfur-containing compound. Mixing of the reaction mixture and/or operating at higher than ambient temperatures will enhance the reaction rate. The weight of the catalyst as a percentage of the total weight of the sulfur-containing compound and alkylene oxide is generally in the range of from 0.01 to 10%, preferably about 0.1 to 3%, and most preferably 0.2 to 1%. The molar ratio of mercaptan to alkylene oxide is from about 1:1 to about 1:20, preferably from about 1:1 to about 1:10, depending on final products desired. The molar ratio of hydrogen sulfide to alkylene oxide is from about 1.1:1 to about 10:1, preferably from 1.2:1 to 4:1.

A solvent also optionally can be used in the preparation of the catalyst or in the reaction medium. The solvent generally is substantially miscible with the base employed. It can be an ether, an alcohol or water. Suitable solvents include methanol, ethanol, propanol, tetrahydrofuran, water, and other similar oxygen-containing solvents.

The molar ratio of the solvent, if employed, to the alkylene oxide is from about 0.001:1 to about 20:1, preferably from about 0.01:1 to about 10:1, and most preferably from 0.02:1 to 1:1.

Generally, following the addition of the mercaptan to the catalyst followed by addition of the alkylene oxide, the mixture is mixed by a suitable means such as stirring and heated to about 50°-150° C., preferably about 60°-100° C.

The heated mixture can be further purified if necessary. This is usually done by conventional separation means such as filtration to remove any impurities or by distillation.

The process of the invention can also be carried out continuously. For example, the contacting of mercaptans with alkylene oxide in the presence of the catalyst can be done by employing continuous stir tank reactors connected in series, packed columns or towers in which the catalyst is supported on a solid support, and other continuous flows that are readily within the realm of one skilled in the art.

The following examples are provided to further illustrate the practice of the invention and are not intended to limit the scope of the invention of the claims.

EXAMPLE I

This example illustrates the preparation of the catalyst used in the invention.

Ethoxylated alcohol (Union Carbide TERGITOL® 15-S-7; 97 g) and 6 g of 50% aqueous NaOH solution was added to a 200 ml flask equipped with thermowell, magnetic stirring bar, and condenser with $N_2$ inlet on top. The mixture under $N_2$ was heated at 80° C. with stirring for 1 hour. The liquid was clear and reddish orange after heating. After cooling, the flask was stoppered. Avoid exposure to air as much as possible.

The catalyst was also prepared the same way as described above except that 47 g of the ethoxylated alcohol and 3 g of NaOH pellets were used. In this case, a slight amount of NaOH did not dissolve in the ethoxylated alcohol.

EXAMPLE II

This example illustrates the preparation of 2-hydroxyethyl n-octyl sulfide using the catalyst made from an ethoxylated alcohol and sodium hydroxide as described in Example I.

To a 250 ml, 3-necked flask equipped with a thermowell, magnetic stirring bar, pressure equalizing addition funnel, and Dewar condenser with $N_2$ inlet on top of condenser was added 73 g (0.5 mole) of n-octyl mercaptan and 1.0 g of the catalyst prepared in Example I (aqueous NaOH and ethoxylated alcohol). Propylene oxide (10 ml) was then added to the mixture. The initial reaction temperature of the stirred reaction mixture was 21° C. No external heating was applied to the reaction mixture. Although the reaction flask was in a heating mantle, the power to it was off. The rate of reaction was monitored by the increase in temperature of the reaction mixture due to the heat of reaction. Table I below shows the temperature of the reaction mixture increased to 74° C. with 36 minutes after propylene oxide was added. The rate of temperature increase was about 1.5° C./min.

TABLE I

| Reaction Rate of the Invention Process | |
|---|---|
| Time (min.) | Temp. (°C.) |
| 0 | 21 |
| 14 | 27 |
| 25 | 39 |
| 32 | 57 |
| 36 | 74 |
| 43 | 73 |

The reaction was completed by slowly adding an additional 25 ml of propylene oxide at rate so that the reaction temperature stayed in the range of 70°-90° C. The heating mantle was removed to allow faster heat loss to maintain the temperature range. The total amount of propylene oxide used was 35 ml or 0.5 mole. After the addition of propylene oxide was completed, the reaction mixture was heated for 1 hour at 75° C. Gas chromatograph (GC) analysis (20 in×⅛ in 2% OV-101 column, oven temperature was 50° C. initially and increased at 15° C./min to 250° C., FID detector) showed that the product was 99% n-octyl mercaptan monopropoxylate (100% yield).

EXAMPLE III

This example is a control process using the catalyst disclosed in the art. The run was carried out exactly the same as that described in Example II except that 1.0 g of a catalyst which was made from 6 g of 50% aqueous NaOH and 97 g of methanol was used. This is a well-known catalyst in the art for the reaction of mercaptans and alkylene oxides. As shown in Table II below, the reaction temperature was only 32° C. after 36 minutes and only 56° C. after 78 minutes of reaction time. The slow rate of temperature increase (0.4° C./minute) was much lower than that of the invention process shown in Example II.

TABLE II

| Reaction Rate of the Referenced Process | |
|---|---|
| Time (min.) | Temp. (°C.) |
| 0 | 20 |
| 15 | 23 |
| 24 | 27 |
| 32 | 30 |
| 36 | 32 |
| 57 | 44 |
| 78 | 56 |

The results shown in Examples II and III demonstrate that the invention process using a catalyst comprising NaOH and an ethoxylated alcohol has much higher reaction rate than the process using a known catalyst, NaOH in methanol, as monitored by the temperature rise with time. The temperature due to the exothermic reaction of n-octyl mercaptan and propylene oxide was 74° C. in 36 minutes for the invention process whereas that was only 32° C. after 36 minutes for the process using NaOH and methanol as catalyst.

Because the reaction with the catalyst comprising NaOH and ethoxylated alcohol started readily, the invention process should prevent runaway reaction where too much alkylene oxide is added before the reaction finally takes off giving a much too exothermic reaction. Also, the better process will allow reactions to proceed at lower temperatures. Reactions at lower temperatures can be useful in obtaining higher selectivity towards the desired products.

EXAMPLE IV

The example is a control process using only NaOH as catalyst and no ethoxylated alcohol or methanol.

The run was carried out exactly the same as that described in Example II except 0.03 g NaOH was used as catalyst. This is the same amount of NaOH that was in 1 g of the catalysts used in Examples II and III. The reaction did not go. The reaction temperature did not change from 21° C. over 2 hours of stirring.

EXAMPLE V

This example illustrates the invention process using a catalyst prepared from anhydrous NaOH and an ethoxylated alcohol. The catalyst was prepared by heating 3 g of NaOH pellets and 47 g of TERGITOL 15-S-7 as described in Example I.

The run was carried out the same as that described in Example II with the exception that only 49.6 g (0.34 mole) of n-octyl mercaptan and 0.3 g of catalyst prepared by heating anhydrous NaOH and TERGITOL® 15-S-7 were used in the reaction and that the mercaptan-catalyst mixture was heated to 79° C. before addition of propylene oxide. After stabilizing at 79° C., power to the heating mantle was turned off, but the reaction flask was left in the mantle. Addition of propylene oxide (2 ml) caused the temperature of the reaction mixture to increase to over 85° C. over 10 minutes. Additional propylene oxide (22 ml) was then added in small portions at a rate so the temperature of the reaction mixture was controlled at 70°–90° C. The heating mantle was removed during this addition to allow faster heat loss. The total amount of propylene oxide added was 24 ml or 0.34 mole. After the addition was completed, the reaction mixture was heated to 80° C. for 0.5 hour. GC analysis showed that the product (70 g, 100% yield) was 99.1% n-octyl mercaptan monopropoxylate.

The results shown in the above examples clearly demonstrate that the present invention is well adapted to carry out the objects and attain the ends and advantages mentioned was well, as those inherent therein. While modifications may be made by those skilled in the art, such modifications are encompassed within the spirit of the present invention as defined by the disclosure and the claims.

That which is claimed is:

1. A process for producing an alkoxylated thio-compound comprising contacting an alkylene oxide with a sulfur-containing compound in the presence of a catalyst under conditions sufficient to synthesize said alkoxylated thio-compound wherein said catalyst comprises a base and an alkoxylated alcohol; and said sulfur-containing compound has the formula of R—SH wherein R is selected from the group consisting of hydrogen, a $C_1$–$C_{10}$ hydrocarbyl radical, and mixtures thereof.

2. A process according to claim 1 wherein said alkoxylated thio-compound has the formula of

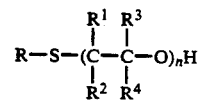

wherein R, $R^1$, $R^2$, $R^3$, and $R^4$ can be the same or different and are each selected from the group consisting of hydrogen, a $C_1$–$C_{20}$ hydrocarbyl radical, and mixtures thereof; and n is a number from 1 to about 20.

3. A process according to claim 2 wherein said alkoxylated thio-compound is selected from the group consisting of 2-mercaptoethanol, 1-mercapto-2-propanol, 2-(ethylthio)ethanol, 2-hydroxyethyl n-octyl sulfide, 2-methyl-2-hydroxypropyl n-octyl sulfide, 2-hydroxybutyl n-octyl sulfide, 2-hydroxyhexyl n-octyl sulfide, 2-hydroxy-3,3-dimethylbutyl n-octyl sulfide, 2-hydroxybutyl n-octyl sulfide, 2-hydroxy-3-methyl-butyl n-octyl sulfide, 2-hydroxypropyl n-octyl sulfide, n-octyl mercaptan monopropoxylate, n-octyl mercaptan diethoxylate, n-octyl mercaptan triethoxylate, t-dodecyl sulfenyl polyethylene oxide having the formula of t—$C_{12}H_{25}$—S—$(CH_2$—$CH_2O)_n$H wherein n is a number from 1 to about 20, and mixtures thereof.

4. A process according to claim 3 wherein said alkoxylated thio-compound is n-octyl mercaptan monopropoxylate.

5. A process according to claim 3 wherein said alkoxylated thio-compound is 1-mercapto-2-propanol.

6. A process according to claim 1 wherein said alkylene oxide has the formula of

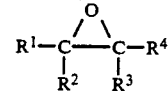

wherein $R^1$, $R^2$, $R^3$ and $R^4$ can be the same or different and are each selected from hydrogen, a $C_1$–$C_{20}$ hydrocarbyl radical, and mixtures thereof.

7. A process according to claim 6 wherein said alkylene oxide is selected from the group consisting of ethylene oxide, propylene oxide, 1,2-epoxycyclohexane, 2-methyl-1,2-epoxypropane, 2,3-epoxybutane, 3-methyl-1,2-epoxybutane, 2-methyl-2,3-epoxybutane, 2,3-epoxyhexane, 3,3-methyl-1,2-epoxybutane, and mixtures thereof.

8. A process according to claim 7 wherein said alkylene oxide is ethylene oxide.

9. A process according to claim 7 wherein said alkylene oxide is propylene oxide.

10. A process according to claim 1 wherein said sulfur-containing compound is selected from the group consisting of hydrogen sulfide, methyl mercaptan, ethyl mercaptan, n-propyl mercaptan, n-butyl mercaptan, t-butyl mercaptan, n-hexyl mercaptan, cyclohexyl mercaptan, n-octyl mercaptan, nonyl mercaptan, t-nonyl mercaptan, n-decyl mercaptan, dodecyl mercaptan, t-dodecyl mercaptan, t-tetradecyl mercaptan, thiophenol, benzyl mercaptan, p-methyl phenyl mercaptan, and mixtures thereof.

11. A process according to claim 10 wherein said sulfur-containing compound is hydrogen sulfide.

12. A process according to claim 10 wherein said sulfur-containing compound is n-octyl mercaptan.

13. A process according to claim 1 wherein said base is selected from the group consisting of an organic base, an inorganic base, and mixtures thereof.

14. A process according to claim 13 wherein said base is selected from the group consisting of tetramethylammonium hydroxide, tetraethylammonium hydroxide, tetrapropylammonium hydroxide, tetramethylammonium bisulfide, tetraethylammonium bisulfide, lithium hydroxide, sodium hydroxide, potassium hydroxide, calcium hydroxide, magnesium hydroxide, sodium bicarbonate, sodium carbonate, sodium oxide, sodium sulfide, sodium bisulfide, magnesium oxide, calcium oxide, calcium carbonate, potassium carbonate, sodium phenoxide, barium phenoxide, calcium phenoxide, $R^5ONa$, $R^5SNa$, and mixtures thereof, wherein $R^5$ is a $C_1$–$C_{18}$ alkyl radical.

15. A process according to claim 14 wherein said base is sodium hydroxide.

16. A process according to claim 1 wherein said alkoxylated alcohol has a general formula of $R^6O)[CH_2CH(R^7)O]_nH$ wherein $R^6$ is a $C_1$–$C_{20}$ hydrocarbyl radical selected from the group consisting of alkyl radical, alkylaryl radical, aryl radical, cycloalkyl radical and alkenyl radical; $R^7$ is selected from the group consisting of hydrogen, $C_1$–$C_{16}$ alkyl radical, and $C_2$–$C_{16}$ alkenyl radical; and n is a number of from 1 to about 20.

17. A process according to claim 16 wherein said alkoxylated alcohol is TERGITOL ® 15-S-7 which is an ethoxylated alcohol surfactant and has the formula of $R^6O(CH_2CH_2O)_7H$, wherein $R^6$ is a secondary alkyl radical having 11 to 15 carbon atoms.

18. A process according to claim 1 wherein the weight ratio of said alkoxylated alcohol to said base is in the range of from about 1:1 to about 1000:1.

19. A process for producing n-octyl mercaptan monopropoxylate comprising contacting propylene oxide with n-octyl mercaptan in the presence of catalyst at 60° C. to 100° C. wherein said catalyst is prepared by heating sodium hydroxide and an ethoxylated alcohol having the formula of $R^6O(CH_2CH_2O)_7H$; wherein $R^6$ is a secondary alkyl radical having 1 to 15 carbon atoms and the weight ratio of said ethoxylated alcohol to sodium hydroxide is in the range of from about 20:1 to about 50:1.

* * * * *